United States Patent
Nomura et al.

(10) Patent No.: US 8,324,141 B2
(45) Date of Patent: Dec. 4, 2012

(54) SURFACTANT COMPOSITION

(75) Inventors: Masato Nomura, Wakayama (JP);
Toshihiro Tanaka, Wakayama (JP);
Takeshi Tomifuji, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/601,221

(22) PCT Filed: Jul. 9, 2008

(86) PCT No.: PCT/JP2008/062770
§ 371 (c)(1),
(2), (4) Date: Dec. 17, 2009

(87) PCT Pub. No.: WO2009/008538
PCT Pub. Date: Jan. 15, 2009

(65) Prior Publication Data
US 2010/0144586 A1   Jun. 10, 2010

(30) Foreign Application Priority Data

Jul. 10, 2007 (JP) ................................ 2007-180802
Apr. 7, 2008 (JP) ................................ 2008-099228

(51) Int. Cl.
*C11D 17/00* (2006.01)
(52) U.S. Cl. ......... 510/130; 510/276; 510/505; 510/506
(58) Field of Classification Search .................. None
See application file for complete search history.

(56) References Cited

U.S. PATENT DOCUMENTS

2005/0106118 A1 * 5/2005 Sakuma et al. ............ 424/70.24

FOREIGN PATENT DOCUMENTS

| CN | 1753981 A | 3/2006 |
|---|---|---|
| DE | 44 36 066 A1 | 4/1996 |
| EP | 0 300 444 A1 | 1/1989 |
| JP | 49-22406 A | 2/1974 |
| JP | 5-97633 A | 4/1993 |
| JP | 2003-292990 A | 10/2003 |

OTHER PUBLICATIONS

Chinese Office Action mailed on Mar. 29, 2011 in Chinese Patent Application No. 200880023897.2 with English translation.
Machine generated English translation of JP 5-97633 A published Apr. 20, 1993.
International Search Report for Application No. PCT/JP2008/062770 mailed on Sep. 2, 2008.
Extended European Search Report issued Mar. 7, 2012, in European Patent Application No. 08791176.4.
Machine generated English translation of JP 5-97633 published Apr. 20, 1993.

* cited by examiner

*Primary Examiner* — Necholus Ogden, Jr.
(74) *Attorney, Agent, or Firm* — Birch, Stewart, Kolasch & Birch, LLP

(57) ABSTRACT

Disclosed is a surfactant composition containing an alkyl sulfate ester salt derivative represented by the following general formula (1). R—O—(PO)$_n$—SO$_3$m (1) (In the formula, R represents a linear alkyl group having 8-24 carbon atoms; PO represents a propyleneoxy group; n represents an average mole number of added PO that is a number satisfying $0<n\leq0.9$; and M represents a cation.)

5 Claims, No Drawings

SURFACTANT COMPOSITION

FIELD OF THE INVENTION

The present invention relates to a novel surfactant composition, and, specifically, to a surfactant composition containing an alkyl sulfate salt derivative having a specified structure.

BACKGROUND OF THE INVENTION

As various nonionic surfactants and anionic surfactants which are commonly used at present, those derived from alcohols originated from petrochemical raw materials or alcohols originated from oil and fats raw materials are known.

As the method of producing alcohols originated from petrochemical raw materials which alcohols are called synthetic alcohols, for example, there is a method in which a compound having an internal olefin is derived by an oligomerization reaction through ethylene and then converted into an alcohol derivative by oxo reaction. It is known that the synthetic alcohol obtained resultantly is a mixture containing about 20% by weight of branched alcohols besides about 80% by weight of linear alcohols. It is known that various surfactants derived from synthetic alcohols have such excellent characteristics that they have a low Krafft point and are not precipitated in hard water as compared with derivatives from linear alcohols.

On the other hand, it is known that various surfactants derived from alcohols originated from oil and fats raw materials which alcohols are one type of natural alcohols have the characteristics such as high foaming ability, foam retaining ability, low cmc, high cloud point and high emulsifying ability compared with surfactants derived from synthetic alcohols.

As mentioned above, the surfactants derived from synthetic alcohols are different from those derived from natural alcohols in properties and performances. Therefore, it is usually necessary to use different surfactants according to the use of the surfactant at present.

There is an increased and worldwide demand for natural alcohols in view of the carbon neutral at present. However, surfactants derived from natural alcohols are inferior to those derived from synthetic alcohols in low temperature stability. Therefore, there is a fear that they have not a little adverse influence on the appearance and performance of a system in which they are blended.

SUMMARY OF THE INVENTION

The present invention relates to a surfactant composition comprising an alkyl sulfate salt derivative represented by the following formula (1):

  (1)

wherein R represents a straight-chain alkyl group having 8 to 24 carbon atoms, PO represents a propylene oxide group, $\overline{n}$ denotes the average number of added moles of PO and is a number satisfying: $0<\overline{n}\leq 0.9$ and M represents a cation.

Also, the present invention relates to a surfactant composition comprising an alkyl sulfate salt derivative represented by the formula (1) which derivative is produced by steps comprising the following steps (A-I) and (A-II):

step (A-I): a step of adding propylene oxide in an amount exceeding 0 mol and 0.9 mol or less to 1 mol of an alcohol having a straight-chain alkyl group having 8 to 24 carbon atoms; and step (A-II): a step of sulfating the alkoxylate obtained in the above (A-I) and neutralizing the resultant;

  (1)

wherein R represents a straight-chain alkyl group having 8 to 24 carbon atoms, PO represents a propylene oxide group, $\overline{n}$ denotes the average number of added moles of PO and is a number satisfying: $0<\overline{n}\leq 0.9$ and M represents a cation.

Also, the present invention relates to a surfactant composition comprising an alkyl sulfate salt derivative (1-1) represented by the following formula (1-1) and an alkyl sulfate salt (2-1) represented by the following formula (2-1), wherein the average number of added moles of propylene oxide in the mixture of the alkyl sulfate salt derivative (1-1) and the alkyl sulfate salt (2-1) exceeds 0 and is 0.9 mol or less based on 1 mol of the alcohol which is the raw material of the above mixture;

  (1-1)

wherein R represents a straight-chain alkyl group having 8 to 24 carbon atoms, PO represents a propylene oxide group, m denotes the average number of added moles of PO and is a number exceeding 0 and M represents a cation;

  (2-1)

wherein R represents a straight-chain alkyl group having 8 to 24 carbon atoms and M represents a cation.

Also, the present invention relates to a surfactant composition comprising an alkyl sulfate salt derivative represented by the formula (1) which derivative is produced by steps comprising the following steps (B-I), (B-II) and (B-III):

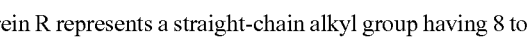  (1)

wherein R represents a straight-chain alkyl group having 8 to 24 carbon atoms, PO represents a propylene oxide group, $\overline{n}$ denotes the average number of added moles of PO and is a number satisfying: $0<\overline{n}\leq 0.9$ and M represents a cation;

step (B-I): a step of adding propylene oxide in an average amount exceeding 0 mol to 1 mol of an alcohol having a straight-chain alkyl group having 8 to 24 carbon atoms;

step (B-II): a step of sulfating the alkoxylate obtained in the above (B-I) and neutralizing the resultant; and step (B-III): a step of blending the alkyl sulfate obtained in the above (B-II) and an alkyl sulfate salt represented by the following formula (2);

  (2)

wherein R represents a straight-chain alkyl group having 8 to 24 carbon atoms and M represents a cation.

Also, the present invention relates to a surfactant composition comprising an alkyl sulfate salt derivative represented by the formula (1) which derivative is produced by steps comprising the following steps (C-I), (C-II) and (C-III):

  (1)

wherein R represents a straight-chain alkyl group having 8 to 24 carbon atoms, PO represents a propylene oxide group, $\overline{n}$ denotes the average number of added moles of PO and is a number satisfying: $0<\overline{n}\leq 0.9$ and M represents a cation;

step (C-I): a step of adding propylene oxide in an average amount exceeding 0 mol to 1 mol of an alcohol having a straight-chain alkyl group having 8 to 24 carbon atoms;

step (C-II): a step of blending the alkoxylate obtained in the above (C-I) with an alcohol represented by the following formula (3);

  (3)

wherein R represents a straight-chain alkyl group having 8 to 24 carbon atoms; and step (C-III): a step of sulfating the above mixture obtained in the above (C-II) and neutralizing them.

Also, the present invention relates to a detergent composition containing the above surfactant composition of the present invention.

Also, the present invention relates to use of the above surfactant composition of the present invention as a detergent composition or a cosmetic composition. The surfactant composition of the present invention may be compounded in various products including detergent compositions such as a body (including a hair use) detergent composition, a clothing detergent composition and hard surface detergent composition and cosmetic compositions.

DETAILED DESCRIPTION OF THE INVENTION

If natural alcohols or their derivatives can impart the same characteristics and performances as synthetic alcohols or their derivatives without losing their excellent characteristics and performances, the use of an alcohol in accordance to the state of affairs of raw materials is largely expected regardless of the purpose and use and therefore, there is currently a strong desire to develop technologies for reforming the properties of natural alcohols and their derivatives.

In view of this situation, the inventors of the present invention have started searching an anionic surfactant composition which is derived from natural alcohols and has the same characteristics as an anionic surfactant derived from a synthetic alcohol with the intention of high utilization of natural alcohols.

Among anionic surfactants, alkyl sulfates obtained through a process of sulfating an alcohol are useful as surfactants used in many uses such as detergent compositions. However, if an alkyl sulfate derived from a natural alcohol can be provided with the performance of an alkyl sulfate derived from a synthetic alcohol characterized by the feature of a low Krafft point and resistance to precipitation in hard water, while retaining the abilities such as high foaming ability and foam retentivity even in the presence of oil stains, it is expected that the range of applications will grow.

The inventors of the present invention have made earnest studies and as a result, found that a surfactant composition containing a specified alkyl sulfate salt derivative is superior in low-temperature stability and stability in hard water and has high foaming ability and foam retentivity.

A surfactant composition according to the present invention and particularly, a surfactant composition containing a specified alkyl sulfate salt derivative is superior in low-temperature stability and stability in hard water and has high foaming ability and foam retentivity even in the presence of oil.

The present invention provides a surfactant composition which contains an alkyl sulfate salt and has the characteristics that it has a low Krafft point and is superior in stability in hard water and also in foaming ability and foam retentivity.

<Surfactant Composition>

The surfactant composition of the present invention contains an alkyl sulfate salt derivative represented by the following formula (1).

Wherein, R represents a straight-chain alkyl group having 8 to 24 carbon atoms, PO represents a propylene oxide group and $\underline{n}$ denotes the average number of added moles of PO and is a number satisfying: $0 < n \leq 0.9$. M represents a cation.

Here, the straight-chain alkyl group represented by R in the formula (1) has preferably 8 to 16, more preferably 10 to 14 and even more preferably 12 to 14 carbon atoms from the viewpoint of the availability of raw materials and handling easiness.

Also, the average number n of added moles of PO in the formula (1) is more preferably 0.1 to 0.9 and even more preferably 0.2 to 0.8 from the viewpoint of performances such as low-temperature stability and stability in hard water.

Also, when R in the formula (1) is a straight-chain alkyl group having 12 carbon atoms, n is preferably 0.1 to 0.8 and more preferably 0.1 to 0.6 from the viewpoint of foam retentivity. When R in the formula (1) is a straight-chain alkyl group having 14 carbon atoms, $\underline{n}$ is preferably 0.4 to 0.9 and more preferably 0.6 to 0.9 from the viewpoint of low-temperature stability and stability in hard water. Also, when R in the formula (1) is a straight-chain alkyl group having 12 carbon atoms and a straight-chain alkyl group having 14 carbon atoms, $\underline{n}$ is preferably 0.1 to 0.9 and more preferably 0.2 to 0.8 from the viewpoint of foam retentivity, low-temperature stability and stability in hard water.

Also, M in the formula (1) is a cationic group forming the salt and represents an alkali metal, alkali earth metal, $NH_4$ or an alkanol ammonium group such as a triethanol ammonium group. Examples of the alkali metal include sodium, potassium and lithium and examples of the alkali earth metal include calcium. Among these metals, sodium, $NH_4$ and potassium are more preferable and sodium is even more preferable.

The surfactant composition of the present invention is produced and distributed in the form of an aqueous solution having a concentration of 30% by weight or less, hydrate paste having a concentration of 60% by weight to 80% by weight or in a powder form obtained after dried. The surfactant composition may be one constituted of an alkyl sulfate salt derivative represented by the formula (1). Also, the alkyl sulfate salt may be arbitrarily diluted, in use, with water or dried to regulate the concentration. In this case, a surfactant composition constituted of an alkyl sulfate salt derivative represented by the formula (1) is provided. Also, the surfactant composition may be one constituted of an alkyl sulfate salt derivative represented by the formula (1) and water.

The alkyl sulfate salt derivative to be used in the surfactant composition of the present invention may be produced, for example, by a production method (production method A) containing the following steps (A-I) and (A-II), though there is no limitation to the method.

Step (A-I): a step of adding propylene oxide in an amount exceeding 0 mol and 0.9 mol or less to 1 mol of an alcohol having a straight-chain alkyl group having 8 to 24 carbon atoms.

Step (A-II): a step of sulfating the alkoxylate obtained in the above (A-I), followed by neutralizing.

The step (A-I) is a step of adding propylene oxide in an average amount exceeding 0 mol and 0.9 mol or less to 1 mol of an alcohol having a straight-chain alkyl group having 8 to 24 carbon atoms to obtain an alkoxylate (propylene oxide addition product of an alcohol). The alkyl group of the alcohol used in the present invention is a straight-chain alkyl group having 8 to 24 carbon atoms and is a straight-chain alkyl group having preferably 8 to 16, more preferably 10 to 14 and even more preferably 12 to 14 carbon atoms from the viewpoint of the availability of raw materials and handling easiness. Also, the average number of added moles of propylene oxide is more preferably 0.1 to 0.9 and even more preferably 0.2 to 0.8 from the viewpoint of performances such as low-temperature stability and stability in hard water.

Also, the amount of the propylene oxide per one mol of the above alcohol is preferably an amount enough to produce an alkyl sulfate salt derivative represented by the formula (1). Specifically, the amount of the propylene oxide exceeds 0 mol and is 0.9 mol or less per one mol of the above alcohol.

As a method used to carry out the step (A-I), a conventionally known method may be used. Specifically, an autoclave is charged with an alcohol and KOH as a catalyst in an amount of 0.5 to 1 mol % of the alcohol. The mixture is heated and dehydrated to add PO by an addition reaction at 130 to 160° C. whereby the alkyl sulfate salt derivative can be produced. The autoclave is preferably provided with a stirrer, a temperature control device and an automatic introduction device.

The step (A-II) is a step of sulfating the alkoxylate obtained in the above (A-I), followed by neutralizing. Examples of the sulfating method include methods using sulfur trioxide (liquid or gas), sulfur trioxide-containing gas, fuming sulfuric acid, chlorosulfonic acid or the like. Particularly, it is preferable to use a method in which sulfur trioxide and the alkoxylate are supplied continuously in a gas or liquid form at the same time from the viewpoint of preventing the generation of waste sulfuric acid and waste hydrochloric acid.

Example of a method of neutralizing the sulfate include a batch system in which the sulfate is added to a specified amount of a neutralizing agent with stirring to neutralize and a continuous system in which the sulfate and a neutralizing agent are continuously supplied to the inside of a pipe to neutralize using a stirring mixer, though there is no limitation to the neutralization method in the present invention. Examples of the neutralizing agent used here include an aqueous alkali metal solution, aqueous alkali earth metal solution, aqueous ammonia and triethanolamine. An aqueous alkali metal solution is preferable and sodium hydroxide is more preferable.

The surfactant composition of the present invention may be a mixture of compounds which each have the structure of the alkyl sulfate salt derivative represented by the above formula (1) and differ in the mole number of added moles of propylene oxide to prepare the mixture as the alkyl sulfate salt derivative. For example, an alkyl sulfate salt to which no propylene oxide is added is blended with an alkyl sulfate salt in which the average number of added moles of propylene oxide exceeds 0 and more preferably 1 or more to obtain a mixture in which the average number $\underline{n}$ of added moles of PO exceeds 0 and is 0.9 mol or less, the obtained mixture being used as the compound of the formula (1) according to the present invention. In this case, as the alkyl sulfate salt in which the average mole number of propylene oxide exceeds 0, an alkyl sulfate salt in which the average number of added moles of propylene oxide is large, for example a number exceeding one, may be used.

Also, in addition to the above methods, a compound obtained in the following manner may be used as the compound represented by the formula (1): an alcohol is blended with an alkoxylate in which the average number of added moles of propylene oxide exceeds 0 and is preferably 1 or more to obtain a mixture in which the average number $\underline{n}$ of added moles of PO exceeds 0 and is 0.9 mol or less, followed by sulfating and neutralizing. In this case, as the alkoxylate in which the average number of added moles of propylene oxide exceeds 0, an alkoxylate in which the average mole number of propylene oxide is large, for example a number exceeding one, may also be used.

Specifically, the alkyl sulfate salt derivative to be used in the surfactant composition of the present invention may be produced by a production method (production method B) containing the following steps (B-I) (B-II) and (B-III) or by a production method (production method C) containing the following steps (C-I), (C-II) and (C-III).

<Production Method B>

Step (B-I): a step of adding propylene oxide in an average amount exceeding 0 mol, and preferably ranging from 1 mol to 6 mol and more preferably ranging from 2 mol to 5 mol to 1 mol of an alcohol having a straight-chain alkyl group having 8 to 24 carbon atoms.

Step (B-II): a step of sulfating the alkoxylate obtained in the above (B-I), followed by neutralizing.

Step (B-III): a step of blending the alkyl sulfate salt obtained in the above (B-II) and an alkyl sulfate salt represented by the following formula (2).

$$R\text{—}O\text{—}SO_3M \quad (2)$$

In the formula, R represents a straight-chain alkyl group having 8 to 24 carbon atoms and M represents a cation.

<Production Method C>

Step (C-I): a step of adding propylene oxide in an average amount exceeding 0 mol, and preferably ranging from 1 mol to 6 mol and more preferably ranging from 2 mol to 5 mol to 1 mol of an alcohol having a straight-chain alkyl group having 8 to 24 carbon atoms.

Step (C-II): a step of blending the alkoxylate obtained in the above (C-I) with an alcohol represented by the following formula (3).

$$R\text{—}O\text{—}H \quad (3)$$

In the formula, R represents a straight-chain alkyl group having 8 to 24 carbon atoms.

Step (C-III): a step of sulfating the above mixture obtained in the above (C-II), followed by neutralizing.

In the production method B, the step (B-I) is a step of adding propylene oxide in an average amount exceeding 0 mol, and preferably ranging from 1 mol to 6 mol and more preferably ranging from 2 mol to 5 mol to 1 mol of an alcohol having a straight-chain alkyl group having 8 to 24 carbon atoms to obtain an alkoxylate (propylene oxide addition product of an alcohol). This step may be carried out in the same manner as the step (A-I) in the above production method A. The step (B-II) is a step of sulfating the alkoxylate obtained in the above (B-I), followed by neutralizing, and may be carried out in the same manner as the step (A-II) of the above production method A. An alkyl sulfate salt (component ($B_1$)) having a higher average number of added moles of propylene oxide is obtained by the step (B-II). The step (B-III) is a step of blending the alkyl sulfate salt obtained in the above (B-II) and an alkyl sulfate salt (component ($B_2$)) represented by the formula (2). The mixture becomes the alkyl sulfate salt derivative represented by the formula (1). Therefore, the component ($B_1$) and the component ($B_2$) are blended such that $\underline{n}$ in the formula (1) exceeds 0 and is 0.9 mol or less.

In the production method C, the step (C-I) is a step of adding propylene oxide in an average amount exceeding 0 mol, and preferably ranging from 1 mol to 6 mol and more preferably ranging from 2 mol to 5 mol to an alcohol having a straight-chain alkyl group having 8 to 24 carbon atoms, to obtain an alkoxylate (propylene oxide addition product of an alcohol). This step may be carried out in the same manner as the step (A-1) in the above production method A. The step (C-II) is a step of blending the alkoxylate (component ($C_1$)) obtained in the above (C-I) with an alcohol (component ($C_2$)) represented by the formula (3), and a neutralized product of the sulfate in the subsequent step (C-III) becomes the alkyl sulfate salt derivative of the formula (1). Therefore, in the step (C-II), the component ($C_1$) and the component ($C_2$) are blended such that $\underline{n}$ in the formula (1) exceeds 0 and is 0.9 mol or less. The step (C-III) is a step of sulfating the above mixture obtained in the above step (C-II), followed by neutralizing and may be carried out in the same manner as the step (A-II) in the above production method A.

The surfactant composition of the present invention may contain an alkyl sulfate salt derivative (1-1) (component (1-1)) represented by the following formula (1-1) and an alkyl sulfate salt (2-1) (component (2-1)) represented by the following formula (2-1), wherein the average number of added moles of propylene oxide in the mixture of the alkyl sulfate salt derivative (1-1) and the alkyl sulfate salt (2-1) exceeds 0 and is 0.9 mol or less based on 1 mol of the alcohol which is the raw material of the above mixture. Specifically, the surfactant composition of the present invention may be prepared by blending the component (1-1) with the component (2-1), and may be one to which propylene oxide is added in an average amount exceeding 0 and of 0.9 mol or less based on 1 mol of the total amount of the alcohol used for the production of the component (1-1) and the alcohol used for the production of the component (1-2). In the above production methods A to C, a composition containing such a mixture is obtained. Preferable R and M in the formulae (I-1) and (2-1) are the same as above. m is an average number of added moles of propylene oxide in the components (1-1) and (2-1) and a number exceeding 0, preferably 1 or more and 6 or less and more preferably 2 or more and 5 or less based on 1 mol of the alcohols which are the raw materials of the above mixture.

$$R\!-\!O\!-\!(PO)_m\!-\!SO_3M \quad (1\text{-}1)$$

Wherein R represents a straight-chain alkyl group having 8 to 24 carbon atoms, PO represents a propylene oxide group, m denotes the average number of added moles of PO and is a number exceeding 0, and is preferably a number of 1 or more and 6 or less and more preferably 2 or more and 5 or less. M represents a cation.

$$R\!-\!O\!-\!SO_3M \quad (2\text{-}1)$$

Wherein R represents a straight-chain alkyl group having 8 to 24 carbon atoms and M represents a cation.

In the present invention, the average number of added moles of propylene oxide may be found from the reaction ratio (charge ratio) of raw materials. Also, the following method may be used to measure.

<Method of Measuring the Average Number of Added Moles of Propylene Oxide>

(1) Sample Preparation

About 30 mg of a perfectly dried measuring sample was weighed under vacuum in a $^1$H-1-NMR sample tube having a diameter of 5 mm and dissolved by adding about 0.5 ml of deuterated solvent. Here, the deuterated solvent is a heavy methanol solvent and the like and an appropriate solvent which can dissolve the sample is selected.

(2) Measurement of NMR and Calculation of the Molar Number of Addition.

The measurement of $^1$H-NMR was made using Mercury 400 manufactured by Varian Technologies Japan Ltd. in normal conditions. The signals derived from a methine group directly connected to a sulfate group are observed at about 4.3 ppm, the signals derived from a methyl group of a propylene oxide chain connected to the propylene oxide chain was observed at about 2.1 ppm and the signals derived from a methyl group of an alkyl chain is observed at about 1.9 ppm. Accordingly, the number of added moles of propylene oxide is calculated by the following calculation formula.

{Average number of added moles of propylene oxide}=(3a/c)+(b/c)

a: Integral value of the signals derived from a methine group of a propylene oxide chain directly connected to a sulfate group which signals are observed at about 4.3 ppm.

b: Integral value of the signals derived from a methyl group of a propylene oxide chain connected to the propylene oxide chain which signals are observed at about 2.1 ppm.

c: Integral values of the signals derived from a methyl group of an alkyl chain which signals are observed at about 1.9 ppm.

The surfactant composition of the present invention has a foam retentivity of preferably 70% or more and more preferably 80% or more, the foam retentivity being able to be found by the following measuring method. This measuring method is a type of the Ross-Miles method.

<Method of Measuring Foam Retentivity>

(A) An aqueous solution of 0.2 wt % (as the concentration of the alkyl sulfate salt derivative represented by the formula (1), that is, the concentration of effective content of a surfactant) of the surfactant composition was prepared (using ion exchange water) and then, 50 mL of the aqueous solution was poured into a cylindrical glass tube (diameter: 5 cm, height: 90 cm) (water temperature: 25° C.

(B) Then, 0.25 g of a mixture solution of triolein (99.5% by weight) and lanolin (0.5% by weight) was added to the solution from above the glass tube in such a manner as to prevent the mixture solution from adhering to the wall surface of the glass tube and then, 200 mL of the aqueous surfactant composition solution was poured into the glass tube for 30 seconds.

(C) The height of foam just after 200 mL of the aqueous solution was added and the height of foam after the solution was allowed to stand for 10 minutes were each measured. The rate of the height of foam after the solution was allowed to stand for 10 minutes to the height of foam just after the aqueous solution was poured was defined as the foam retentivity (%) of the surfactant composition. This foam retentivity is calculated according to the following equation.

Foam retentivity (%)=The height of foam after the solution is allowed to stand for 10 minutes (mm)/ the height of foam just after the aqueous solution is added×100.

<Detergent Composition>

The surfactant composition of the present invention has the characteristic that it is superior in low-temperature stability, stability in hard water, foaming ability and foaming retentivity. Therefore, the surfactant composition of the present invention may be compounded in various products such as detergent compositions and cosmetic compositions corresponding to the use and object of each product. Examples of the detergent composition include body (including a hair use) detergent compositions, clothing detergent compositions and hard surface detergent compositions.

The content (as the concentration of the alkyl sulfate salt derivative represented by the formula (1), that is, the concentration of effective content of a surfactant) of the surfactant composition of the present invention is preferably 0.5 to 27% by weight, more preferably 1 to 25% by weight, even more preferably 5 to 25% by weight and even more preferably 5 to 20% by weight in the detergent composition, though no particular limitation is imposed on it.

Besides the surfactant composition of the present invention, various additives which are usually used in the fields concerned may be optionally blended corresponding to objects therefore, respectively. These additives include surfactants which are usually (anionic surfactants except for the anionic surfactants of the present invention, nonionic surfactants, amphoteric surfactants and cationic surfactants); viscosity regulating agents; foaming agents; higher alcohols and higher fatty acids; various cationic, anionic or nonionic polymers; silicones; polyols; pearling agents; alkali agents; sequestering agents; antiseptics; perfumes; dyes; and inorganic salts.

EXAMPLES

The following examples explain the embodiments of the present invention. These embodiments explain examples of the present invention. However, these examples are not intended to be limiting of the present invention.

Example 1

An autoclave equipped with a stirrer, a temperature-control device and an automatic introduction device was charged with 3447 g of a linear alcohol having 12 carbon atoms [trade name: kalcol 2098 manufactured by Kao corporation] and 5.2 g of KOH, which was then dehydrated at 110° C. under a pressure of 1.3 kPa for 30 minutes. After the alcohol was dehydrated, the atmosphere in the autoclave was replaced with nitrogen. After the alcohol was raised to 120° C., 215 g of propylene oxide was charged in the autoclave. The mixture was subjected to an addition reaction and aging carried out at 120° C. and the reaction mixture was cooled to 80° C. and unreacted propylene oxide was removed under a pressure of 4.0 kPa. After the above unreacted propylene oxide was removed, 5.6 g of acetic acid was added in the autoclave and the resulting mixture was stirred at 80° C. for 30 minutes. Then, the mixture was discharged to obtain an alkoxylate in which the average number of added moles of propylene oxide was 0.2.

The obtained alkoxylate was sulfated using $SO_3$ gas in a falling film reactor (hereinafter referred to as FFR). The obtained sulfate was neutralized by an aqueous NaOH solution to obtain a composition containing an alkyl sulfate salt derivative. With regard to the obtained surfactant composition, the Krafft point and stability in hard water (Stability in hard water) were measured in the methods shown below. Also, the foam retentivity was calculated in the above method. The results of evaluation are shown in Table 1.
<Krafft Point>

An aqueous 1 wt % surfactant composition solution (30 g) was cooled until it was clouded once and then, the temperature of the solution was raised gradually. The temperature at which the appearance of the solution was changed to a transparent solution was defined as the Krafft point. The concentration of this aqueous solution is the concentration of the alkyl sulfate salt derivative represented by the formula (1), that is the concentration of the effective content of the surfactant.
<Stability in Hard Water>

An aqueous 0.5 wt % calcium chloride solution was added to an aqueous 0.5 wt % surfactant composition solution (20 g) at a rate of 1 g/min for titration to measure the titer (mg/g) when the appearance began clouding as the index of evaluation of the stability in hard water. The concentration of this aqueous solution is the concentration of the alkyl sulfate salt derivative represented by the formula (1), that is, the concentration of the effective content of the surfactant.

Example 2

A composition containing an alkyl sulfate salt derivative in which the average number of added moles of propylene oxide was 0.4 was obtained in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 1.

Example 3

A composition containing an alkyl sulfate salt derivative in which the average number of added moles of propylene oxide was 0.6 was obtained in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 1.

Example 4

A composition containing an alkyl sulfate salt derivative in which the average number of added moles of propylene oxide was 0.8 was obtained in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 1.

Comparative Example 1

A sodium alkylsulfate (trade name: Emal 0, manufactured by Kao Corporation) using a natural alcohol derived from oil and fats as raw materials was used to evaluate in the same manner as in Example 1. The results are shown in Table 1.

Comparative Example 2

A composition containing an alkyl sulfate salt derivative in which the average number of added moles of propylene oxide was 1.0 was obtained in the same method as in Example 1. The obtained composition containing an alkyl sulfate salt derivative was used to evaluate in the same manner as in Example 1. The results are shown in Table 1.

Comparative Example 3

A composition containing an alkyl sulfate salt derivative in which the average number of added moles of propylene oxide was 2.0 was obtained in the same method as in Example 1. The obtained composition containing an alkyl sulfate salt derivative was used to evaluate in the same manner as in Example 1. The results are shown in Table 1.

TABLE 1

| | | structure of formula(1) | | | | | Stability in | Foam |
| | | R | | | | | | |
| | | Number of carbons | Branched ratio (%) | n | M | Krafft point (° C.) | hard water (mg/g) | retentivity (%) |
|---|---|---|---|---|---|---|---|---|
| Example | 1 | 12 | 0 | 0.2 | Sodium | 15 | 23000 | 84 |
| | 2 | 12 | 0 | 0.4 | Sodium | 13 | 39000 | 84 |
| | 3 | 12 | 0 | 0.6 | Sodium | 11 | 165000 | 80 |
| | 4 | 12 | 0 | 0.8 | Sodium | 9 | Exceeding 250000 | 74 |
| Comparative example | 1 | 12 | 0 | 0 | Sodium | 18 | 16000 | 76 |
| | 2 | 12 | 0 | 1.0 | Sodium | 7 | Exceeding 250000 | 65 |
| | 3 | 12 | 0 | 2.0 | Sodium | Less than 0 | Exceeding 250000 | 55 |

In this test, a test sample was rated as good when it had a Krafft point of 15° C. or less, stability in hard water of 20000 mg/g or more and a foam retentivity of 70% or more (the same as follows).

Example 5

An alkoxylate in which the average number of added moles of propylene oxide was 0.4 was obtained in the same method as in Example 1. The obtained alkoxylate was sulfated using SO$_3$ gas in a falling film reactor (hereinafter referred to as FFR). The obtained sulfate was neutralized by an aqueous NH$_3$ solution to obtain a composition containing an alkyl sulfate salt derivative. Here, the average number of added moles of propylene oxide was confirmed by the above method using NMR. The obtained composition containing an alkyl sulfate salt derivative was used to evaluate in the same manner as in Example 1. The results are shown in Table 2.

Comparative Example 4

A linear alcohol having 12 carbon atoms (trade name: Kalcol 2098, manufactured by Kao Corporation) was sulfated using SO$_3$ gas in a falling film reactor (hereinafter referred to as FFR). The obtained sulfate was neutralized by an aqueous NH$_3$ solution to obtain a composition containing an alkyl sulfate salt derivative. The obtained composition containing an alkyl sulfate salt derivative was used to evaluate in the same manner as in Example 1. The results are shown in Table 2.

Comparative Example 5

A linear alcohol having 12 carbon atoms (trade name: Kalcol 2098, manufactured by Kao Corporation) was used to obtain an alkoxylate in which the average number of added moles of propylene oxide was 2.0 in the same method as in Example 1. Then, this alkoxylate was sulfated using SO$_3$ gas in a falling film reactor (hereinafter referred to as FFR). The obtained sulfate was neutralized by an aqueous NH$_3$ solution to obtain a composition containing an alkyl sulfate salt derivative. The obtained composition containing an alkyl sulfate salt derivative was used to evaluate in the same manner as in Example 1. The results are shown in Table 2.

TABLE 2

| | | Structure in the formula (1) | | | | | Stability in | Foam |
| | | R | | | | | | |
| | | Number of carbons | Branched ratio (%) | n | M | Krafft point (° C.) | hard water (mg/g) | retentivity (%) |
|---|---|---|---|---|---|---|---|---|
| Example | 5 | 12 | 0 | 0.4 | Ammonium | 8 | 43000 | 86 |
| Comparative example | 4 | 12 | 0 | 0 | Ammonium | 16 | 17000 | 78 |
| | 5 | 12 | 0 | 2.0 | Ammonium | Less than 0 | Exceeding 250000 | 59 |

Example 6

A linear alcohol having 14 carbon atoms (trade name: Kalcol 40.98, manufactured by Kao Corporation) was used to obtain a composition containing an alkyl sulfate salt derivative in which the average number of added moles of propylene oxide was 0.8 in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 3.

Comparative Example 6

A linear alcohol having 14 carbon atoms (trade name: Kalcol 4098, manufactured by Kao Corporation) was sulfated using SO$_3$ gas in a falling film reactor (hereinafter referred to as FFR). The obtained sulfate was neutralized by an aqueous NaOH solution to obtain a composition containing an alkyl sulfate salt derivative. The obtained composition containing an alkyl sulfate salt derivative was used to evaluate in the same manner as in Example 1. The results are shown in Table 3.

Comparative Example 7

A linear alcohol having 14 carbon atoms (trade name: Kalcol 4098, manufactured by Kao Corporation) was used to obtain an alkoxylate in which the average number of added moles of propylene oxide was 2.0 in the same method as in Example 1. Then, this alkoxylate was sulfated using $SO_3$ gas in a falling film reactor (hereinafter referred to as FFR). The obtained sulfate was neutralized by an aqueous NaOH solution to obtain a composition containing an alkyl sulfate salt derivative. The obtained composition containing an alkyl sulfate salt derivative was used to evaluate in the same manner as in Example 1. The results are shown in Table 3.

TABLE 3

| | Structure in the formula (1) | | | | Krafft point (° C.) | Stability in hard water (mg/g) | Foam retentivity (%) |
|---|---|---|---|---|---|---|---|
| | R | | | | | | |
| | Number of carbon atoms | Branched ratio (%) | n | M | | | |
| Example 6 | 14 | 0 | 0.8 | Sodium | 15 | 21000 | 86 |
| Comparative example 6 | 14 | 0 | 0 | Sodium | 29 | 0 | 79 |
| Comparative example 7 | 14 | 0 | 2.0 | Sodium | 12 | Exceeding 250000 | 60 |

Example 7

A composition containing an alkyl sulfate salt derivative in which the average number of added moles of propylene oxide was 2 was obtained in the same method as in Example 1. This composition was blended with a sodium alkyl sulfate (trade name: Emal 0, manufactured by Kao Corporation) in a ratio by mol of 10:90 to obtain a composition containing an alkyl sulfate salt derivative in which the average number of added moles of propylene oxide was 0.2 was obtained. Here, the average number of added moles of propylene oxide was confirmed by the above method using NMR. The obtained composition containing an alkyl sulfate salt derivative was used to evaluate in the same manner as in Example 1. The results are shown in Table 4.

Example 8

A composition containing an alkyl sulfate salt derivative in which the average number of added moles of propylene oxide was 2 was obtained in the same method as in Example 1. This composition was blended with a sodium alkyl sulfate (trade name: Emal 0, manufactured by Kao Corporation) in a ratio by mol of 20:80 to obtain a composition containing an alkyl sulfate salt derivative in which the average number of added moles of propylene oxide was 0.4 was obtained. Here, the average number of added moles of propylene oxide was confirmed by the above method using NMR. The obtained composition containing an alkyl sulfate salt derivative was used to evaluate in the same manner as in Example 1. The results are shown in Table 4.

Example 9

A composition containing an alkyl sulfate salt derivative in which the average number of added moles of propylene oxide was 2 was obtained in the same method as in Example 1. This composition was blended with a sodium alkyl sulfate (trade name: Emal 0, manufactured by Kao Corporation) in a ratio by mol of 30:70 to obtain a composition containing an alkyl sulfate salt derivative in which the average number of added moles of propylene oxide was 0.6. Here, the average number of added moles of propylene oxide was confirmed by the above method using NMR. The obtained composition containing an alkyl sulfate salt derivative was used to evaluate in the same manner as in Example 1. The results are shown in Table 4.

Example 10

A composition containing an alkyl sulfate salt derivative in which the average number of added moles of propylene oxide was 2 was obtained in the same method as in Example 1. This composition was blended with a sodium alkyl sulfate (trade name: Emal 0, manufactured by Kao Corporation) in a ratio by mol of 40:60 to obtain a composition containing an alkyl sulfate salt derivative in which the average number of added moles of propylene oxide was 0.8. Here, the average number of added moles of propylene oxide was confirmed by the above method using NMR. The obtained composition containing an alkyl sulfate salt derivative was used to evaluate in the same manner as in Example 1. The results are shown in Table 4.

Comparative Example 8

A composition containing an alkyl sulfate salt derivative in which the average number of added moles of propylene oxide was 2 was obtained in the same method as in Example 1. This composition was blended with a sodium alkyl sulfate (trade name: Emal 0, manufactured by Kao Corporation) in a ratio by mol of 50:50 to obtain a composition containing an alkyl sulfate salt derivative in which the average number of added moles of propylene oxide was 1.0. Here, the average number of added moles of propylene oxide was confirmed by the above method using NMR. The obtained composition containing an alkyl sulfate salt derivative was used to evaluate in the same manner as in Example 1. The results are shown in Table 4.

TABLE 4

| | | Structure in the formula(1) | | | | | Stability in | Foam |
| | | R | | | | | | |
| | | Number of carbon atoms | Branched ratio (%) | n | M | point (° C.) | hard water (mg/g) | retentivity (%) |
|---|---|---|---|---|---|---|---|---|
| Example | 7 | 12 | 0 | 0.2 | Sodium | 12 | 23000 | 83 |
| | 8 | 12 | 0 | 0.4 | Sodium | 10 | 27000 | 82 |
| | 9 | 12 | 0 | 0.6 | Sodium | 9 | 33000 | 80 |
| | 10 | 12 | 0 | 0.8 | Sodium | 8 | 37000 | 76 |
| Comparative | 1 | 12 | 0 | 0 | Sodium | 18 | 16000 | 76 |
| example | 8 | 12 | 0 | 1.0 | Sodium | 6 | 39000 | 66 |

The results of Comparative Example 1 are described together in Table 4 for reference.

Example 11

A composition containing an alkyl sulfate salt derivative in which the average number of added moles of propylene oxide was 5 was obtained in the same method as in Example 1. This composition was blended with a sodium alkyl sulfate (trade name: Emal 0, manufactured by Kao Corporation) in a ratio by mol of 8:92 to obtain a composition containing an alkyl sulfate salt derivative in which the average number of added moles of propylene oxide was 0.4. Here, the average number of added moles of propylene oxide was confirmed by the above method using NMR. The obtained composition containing an alkyl sulfate salt derivative was used to evaluate in the same manner as in Example 1. The results are shown in Table 5.

Example 12

A composition containing an alkyl sulfate salt derivative in which the average number of added moles of propylene oxide was 5 was obtained in the same method as in Example 1. This composition was blended with a sodium alkyl sulfate (trade name: Emal 0, manufactured by Kao Corporation) in a ratio by mol of 12:88 to obtain a composition containing an alkyl sulfate salt derivative in which the average number of added moles of propylene oxide was 0.6. Here, the average number of added moles of propylene oxide was confirmed by the above method using NMR. The obtained composition containing an alkyl sulfate salt derivative was used to evaluate in the same manner as in Example 1. The results are shown in Table 5.

Example 13

A composition containing an alkyl sulfate salt derivative in which the average number of added moles of propylene oxide was 5 was obtained in the same method as in Example 1. This composition was blended with a sodium, alkyl sulfate (trade name: Emal 0, manufactured by Kao Corporation) in a ratio by mol of 16:84 to obtain a composition containing an alkyl sulfate salt derivative in which the average number of added moles of propylene oxide was 0.8. Here, the average number of added moles of propylene oxide was confirmed by the above method using NMR. The obtained composition containing an alkyl sulfate salt derivative was used to evaluate in the same manner as in Example 1. The results are shown in Table 5.

Comparative Example 9

A composition containing an alkyl sulfate salt derivative in which the average number of added moles of propylene oxide was 5 was obtained in the same method as in Example 1. This composition was blended with a sodium alkyl sulfate (trade name: Emal 0, manufactured by Kao Corporation) in a ratio by mol of 20:80 to obtain a composition containing an alkyl sulfate salt derivative in which the average number of added moles of propylene oxide was 1.0. Here, the average number of added moles of propylene oxide was confirmed by the above method using NMR. The obtained composition containing an alkyl sulfate salt derivative was used to evaluate in the same manner as in Example 1. The results are shown in Table 5.

TABLE 5

| | | Structure in the formula(1) | | | | | Stability in | Foam |
| | | R | | | | | | |
| | | Number of carbon atoms | Branched ratio (%) | n | M | Krafft point (° C.) | hard water (mg/g) | retentivity (%) |
|---|---|---|---|---|---|---|---|---|
| Example | 11 | 12 | 0 | 0.4 | Sodium | 15 | 23000 | 78 |
| | 12 | 12 | 0 | 0.6 | Sodium | 15 | 25000 | 75 |
| | 13 | 12 | 0 | 0.8 | Sodium | 13 | 26000 | 71 |
| Comparative | 1 | 12 | 0 | 0 | Sodium | 18 | 16000 | 76 |
| example | 9 | 12 | 0 | 1.0 | Sodium | 11 | 27000 | 63 |

The results of Comparative Example 1 are described together in Table 5 for reference.

Example 14

An alkoxylate in which the average number of added moles of propylene oxide was 2 was obtained in the same method as in Example 1. This composition was blended with a linear alcohol having 12 carbon atoms (trade name: Kalcol 2098, manufactured by Kao Corporation) in a ratio by mol of 20:80 to obtain an alkoxylate in which the average number of added moles of propylene oxide was 0.4. Then, a composition containing an alkyl sulfate salt derivative was obtained in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 6.

Comparative Example 10

An alkoxylate in which the average number of added moles of propylene oxide was 2 was obtained in the same method as in Example 1. This composition was blended with a linear alcohol having 12 carbon atoms (trade name: Kalcol 2098, manufactured by Kao Corporation) in a ratio by mol of 50:50 to obtain an alkoxylate in which the average number of added moles of propylene oxide was 1.0. Then, a composition containing an alkyl sulfate salt derivative was obtained in the same method as in Example 1. Here, the average number of added moles of propylene oxide was confirmed by the above method using NMR. The obtained composition containing an alkyl sulfate salt derivative was used to evaluate in the same manner as in Example 1. The results are shown in Table 6.

lene oxide was added, to obtain sodium alkyl sulfate. Using the obtained sodium alkylsulfate, it was evaluated in the same manner as in Example 1. The results are shown in Table 7.

Reference Example 2

A synthetic alcohol (trade name: SAFOL 23, manufactured by SASOL, having alkyl groups having 12 and 13 carbon atoms) was sulfated and neutralized by the same method that was shown in Example 1 except that no propylene oxide was added, to obtain sodium alkyl sulfate. Using the obtained sodium alkylsulfate, it was evaluated in the same manner as in Example 1. The results are shown in Table 7.

Reference Example 3

A synthetic alcohol (trade name: ISOFOL 12, manufactured by SASOL, having alkyl groups having 12 carbon

TABLE 6

| | Structure in the formula(1) | | | | | Stability in | Foam |
| | R | | | | | | |
| | Number of carbon atoms | Branched ratio (%) | n | M | Krafft point (° C.) | hard water (mg/g) | retentivity (%) |
|---|---|---|---|---|---|---|---|
| Example 14 | 12 | 0 | 0.4 | Sodium | 10 | 27000 | 83 |
| Comparative 1 | 12 | 0 | 0 | Sodium | 18 | 16000 | 76 |
| example 10 | 12 | 0 | 1.0 | Sodium | 7 | 40000 | 66 | atoms) was sulfated and neutralized by the same method that was shown in Example 1 except that no propylene oxide was added, to obtain sodium alkyl sulfate. Using the obtained sodium alkylsulfate, it was evaluated in the same manner as in Example 1. The results are shown in Table 7.

TABLE 7

| | | structure in the formula(1) | | | | Stability in | Foam |
| | | R | | | | | |
| | | Number of cabon atoms | Branched ratio (%) | n | M | Krafft point (° C.) | hard water (mg/g) | retentivity (%) |
|---|---|---|---|---|---|---|---|---|
| Reference example | 1 | Mixture of alkyl groups having 12carbon atoms and 13 carbon atoms | 20 | 0 | Sodium | 19 | 17000 | 86 |
| | 2 | Mixture of alkyl groups having 12carbon atoms and 13 carbon atoms | 50 | 0 | Sodium | 10 | 36000 | 86 |
| | 3 | 12 | 100 | 0 | Sodium | Less than 0 | Exceeding 250000 | 12 |

The results of Comparative Example 1 are described together in Table 6 for reference.

Reference Example 1

A synthetic alcohol (trade name: NEODOL 23, manufactured by Shell Co., Ltd., having alkyl groups having 12 and 13 carbon atoms) was sulfated and neutralized by the same method that was shown in Example 1 except that no propy- The compositions containing the alkyl sulfate salt derivative of the present invention have high foam retentivity similarly to a sulfate of a natural alcohol as shown in Tables 1 to 6, and also, have a low Krafft point and high stability in hard water similarly to a sulfate of a synthetic alcohol as shown in Table 7. Therefore, it is expected that stability in the formulation of a product can be outstandingly improved. The present invention is also very interesting from the viewpoint of the carbon neutral and may be placed as a high degree of utilization of natural alcohols.

The invention claimed is:

1. A detergent composition comprising a surfactant composition, said surfactant composition comprising an alkyl sulfate salt derivative represented by the following formula (1):

$$R\text{—}O\text{—}(PO)_n\text{—}SO_3M \tag{1}$$

wherein R represents a straight-chain alkyl group having 12 to 14 carbon atoms, PO represents a propylene oxide group, "n" denotes the average number of added moles of PO and is a number satisfying: 0.1 to 0.8 and M represents a cation; wherein the surfactant composition has a Kraft point of 15° C. or less, a stability in hard water of 20,000 mg/g or more, and a foam retentivity of 70% or more.

2. A detergent composition comprising a surfactant composition, said surfactant composition comprising an alkyl sulfate salt derivative (1-1) represented by the following formula (1-1) and an alkyl sulfate salt (2-1) represented by the following formula (2-1), wherein the average number of added moles of propylene oxide in the mixture of the alkyl sulfate salt derivative (1-1) and the alkyl sulfate salt (2-1) is 0.1 to 0.8 mol based on 1 mol of the alcohol which is the raw material of the above mixture;

$$R\text{—}O\text{—}(PO)_m\text{—}SO_3M \tag{1-1}$$

wherein R represents a straight-chain alkyl group having 12 to 14 carbon atoms, PO represents a propylene oxide group, m denotes the average number of added moles of PO and is a number exceeding 0 and M represents a cation;

$$R\text{—}O\text{—}SO_3M \tag{2-1}$$

wherein R represents a straight-chain alkyl group having 8 to 14 carbon atoms and M represents a cation; wherein the surfactant composition has a Kraft point of 15° C. or less, a stability in hard water of 20,000 mg/g or more, and a foam retentivity of 70% or more.

3. The surfactant detergent composition as claimed in claim 1, said composition further comprising water.

4. The detergent composition as claimed in claim 2, said composition further comprising water.

5. The detergent composition as claimed in claim 1, wherein the surfactant composition has 0.5 to 27% by weight of said alkyl sulfate salt derivative represented by formula (1).

* * * * *